(12) United States Patent
Lifshitz et al.

(10) Patent No.: US 6,482,642 B2
(45) Date of Patent: Nov. 19, 2002

(54) TESTING KIT AND METHODOLOGY FOR TESTING FOR THE PRESENCE OF MICROORGANISMS

(75) Inventors: Ran Lifshitz, Willowdale (CA); Donald L. Lush, Caledon East (CA)

(73) Assignee: Environmental Biodetection Products.com, Brampton (CA)

( * ) Notice: Subject to any disclaimer, the term of this patent is extended or adjusted under 35 U.S.C. 154(b) by 0 days.

(21) Appl. No.: 09/821,625

(22) Filed: Mar. 29, 2001

(65) Prior Publication Data

US 2002/0142365 A1 Oct. 3, 2002

(51) Int. Cl.7 ............................................. C12M 1/34
(52) U.S. Cl. ............................ 435/287.6; 435/288.2; 435/304.2
(58) Field of Search ...................... 435/30, 33, 37, 435/34, 39, 40, 287.1, 287.3, 287.4, 287.6, 288.4, 288.5, 288.7, 304.2, 305.2, 305.3, 309.1, 810; 422/100, 102, 58; 436/180, 808, 809

(56) References Cited

U.S. PATENT DOCUMENTS

| | | | | |
|---|---|---|---|---|
| 3,036,894 A | * | 5/1962 | Forestiere | 206/484 |
| 3,666,631 A | * | 5/1972 | Rich et al. | 435/287.6 |
| RE29,725 E | * | 8/1978 | Johnson et al. | 206/219 |
| 4,129,483 A | * | 12/1978 | Bochner | 435/243 |
| 4,708,850 A | * | 11/1987 | Husain | 422/102 |
| 4,906,566 A | | 3/1990 | Cullimore et al. | |
| 5,145,786 A | | 9/1992 | Bailey et al. | 435/252.4 |
| 5,202,262 A | | 4/1993 | Lemonnier | |
| 5,340,747 A | | 8/1994 | Eden | |
| 5,356,815 A | | 10/1994 | Ciotti | |
| 5,643,743 A | | 7/1997 | Chang et al. | |
| 6,022,698 A | | 2/2000 | Chen et al. | |
| 6,051,394 A | | 4/2000 | Simmons et al. | |
| 6,068,988 A | | 5/2000 | Schabert et al. | 435/21 |

FOREIGN PATENT DOCUMENTS

| | | | |
|---|---|---|---|
| EP | 0 872 545 A1 | * | 10/1998 |
| WO | WO 97/14034 | | 4/1997 |
| WO | WO 98/53301 | | 11/1998 |
| WO | WO 0023189 A1 | | 4/2000 |

* cited by examiner

Primary Examiner—William H. Beisner
(74) Attorney, Agent, or Firm—Hodgson Russ LLP

(57) ABSTRACT

A testing kit to determine the presence of microorganisms in aqueous solutions and suspensions by means of using a hand held plastic bag containing at least one reaction chamber, wherein the kit is typically embodied with of plurality of reaction chambers, and wherein each of the reaction chambers may be differently embodied yet still prevent cross contamination between the plurality of reaction chambers contained in the plastic bag.

19 Claims, 4 Drawing Sheets

TESTING KIT AND METHODOLOGY FOR TESTING FOR THE PRESENCE OF MICROORGANISMS

BACKGROUND OF THE INVENTION

The present invention relates to testing kits designed to be used to test for the presence of microorganisms in aqueous solutions and suspensions. Water, one of society's most important resources, is essential for the life of humans and animals. At times, however, water and foods containing deleterious microorganisms can be hazardous.

Many people every year are sickened, or worse yet, die due to consuming water and foods contaminated with microorganisms such as *E. coli* and salmonella. This is true for people who rely on well water as their source of drinking water, as well as for as people who drink water provided by a public utility. People are even sickened by playing in recreational waters containing harmful microorganisms. Hazardous microorganisms are a constant threat to humans and animals alike.

Present testing kits which test for microorganisms have numerous shortcomings. They test for one type of microorganism, while potentially missing many others. This gives a false sense of security to someone about to consume the suspect water or food material which has been tested with one of these devices and given the "all safe" signal. The individual might think the water or food is free of *E. coli* since the test detected no presence of this bacteria, while at the same time the water is loaded with salmonella bacteria. Further, some of the present devices are complicated and expensive to manufacture.

There is a need for a reliable, inexpensive, easy to use testing kit for detecting the presence of either a single or a plurality of microorganisms.

SUMMARY OF THE INVENTION

A testing kit to determine the presence of microorganisms in aqueous solutions, and to determine the presence of microorganisms in suspensions. The testing kit has a hand held apparatus containing at least one reaction chamber. Each reaction chamber contains a reactive agent to test for a predetermined microorganism or group of microorganisms. Each reaction chamber also prevents cross contamination between the plurality of reaction chambers, if any, contained in the plastic bag.

DETAILED DESCRIPTION

Definitions

Figure 1:
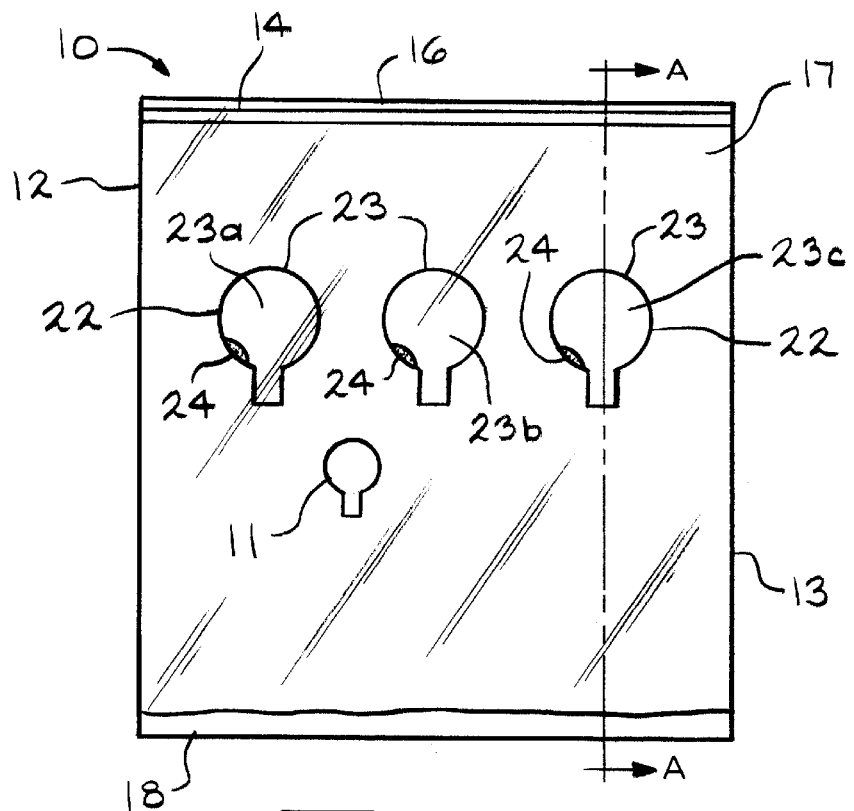
FIG. 1 shows a perspective view of an embodiment of the testing kit.

1. Microorganisms 110 include bacteria, the coliform group of bacteria, the *E. coli* group of bacteria, salmonella bacteria, listeria, fungi, yeasts, molds (which are taxonomically fungi and yeasts), viruses, fecal streptococcus, enterococcus, iron bacteria, sulphur bacteria, *Vibro cholerae*, and other microorganisms 110 well known to those skilled in the art.

2. Reactive Agent 24 includes chromogens, chromogenic substrates, and chromogenic reactive agents. Reactive agents 24 may change color when mixed with microorganisms 110, or materials excreted by microorganisms. Reactive agents are well known to those skilled in the art.

3. Test Mixture 56 includes the aqueous solution to be tested 20, the suspension to be tested 100, or a mixture of the solution 20 and suspension 100 with the reactive agent 24.

Figure 2:
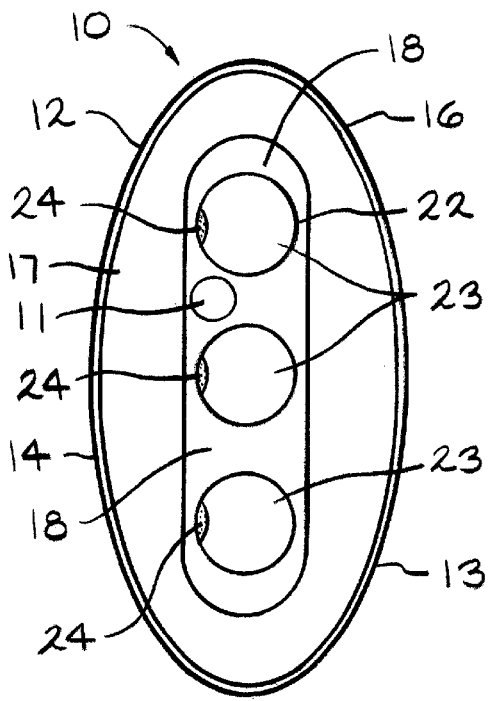
FIG. 2 shows a top plan of the testing kit of FIG. 1.
Figure 3:
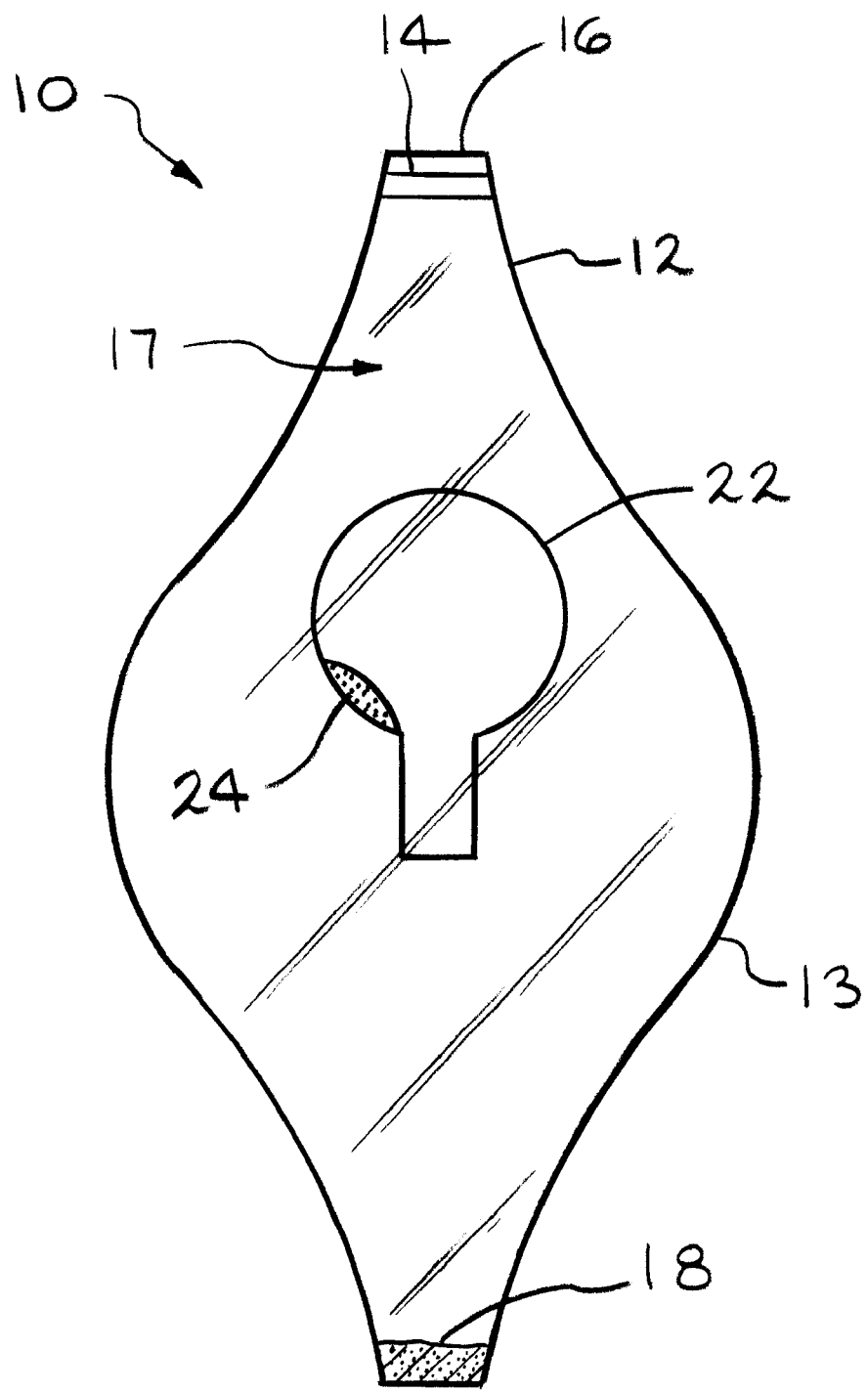
FIG. 3 shows a sectional view of the testing kit taken along line A—A of FIG. 1.

FIG. 1 shows a side perspective view of the testing kit 10. The testing kit 10 is a container 12 which may be embodied in the form of a plastic bag 13 defining a bag interior 17 therein, as show in FIGS. 1–4. The plastic bag 13 allows the entire testing kit to be compactly contained, folded, and stored. The plastic bag 13 also allows the user to visually observe what is occurring in the bag interior 17. The plastic bag 13 has a resealable opening 14 along an edge 16 thereof. That is, it may be repeatedly opened and closed by pulling the resealable opening 14 apart, and then compressing and or folding the resealable opening 14 together again. This type of plastic bag 13 is well known to those skilled in the art. FIG. 2 shows a top plan view of the testing kit 10 with the resealable opening 14 of the plastic bag 13 in the open position. FIG. 3 shows a sectional view of the testing kit 10 taken along line A—A of FIG. 1. The testing kit 10 provides a quick, inexpensive and reliable way to test for the presence of microorganisms 110 (FIG. 4), which may or may not be present in an aqueous solution to be tested 20, or a suspension to be tested 100, as fully described below.

A medium 18 is disposed in the bag interior 17 of the container 12. The medium 18, when mixed with an aqueous solution and/or suspension containing microorganisms 110 promotes and fosters the growth of microorganisms 110, and is nutrient rich to serve this purpose. Currently there are hundreds of different mediums 18 on the market, and they may be in the form of pastes, pellets, powders, liquids, and combinations thereof, and are well known to those skilled in the art.

Figure 4:
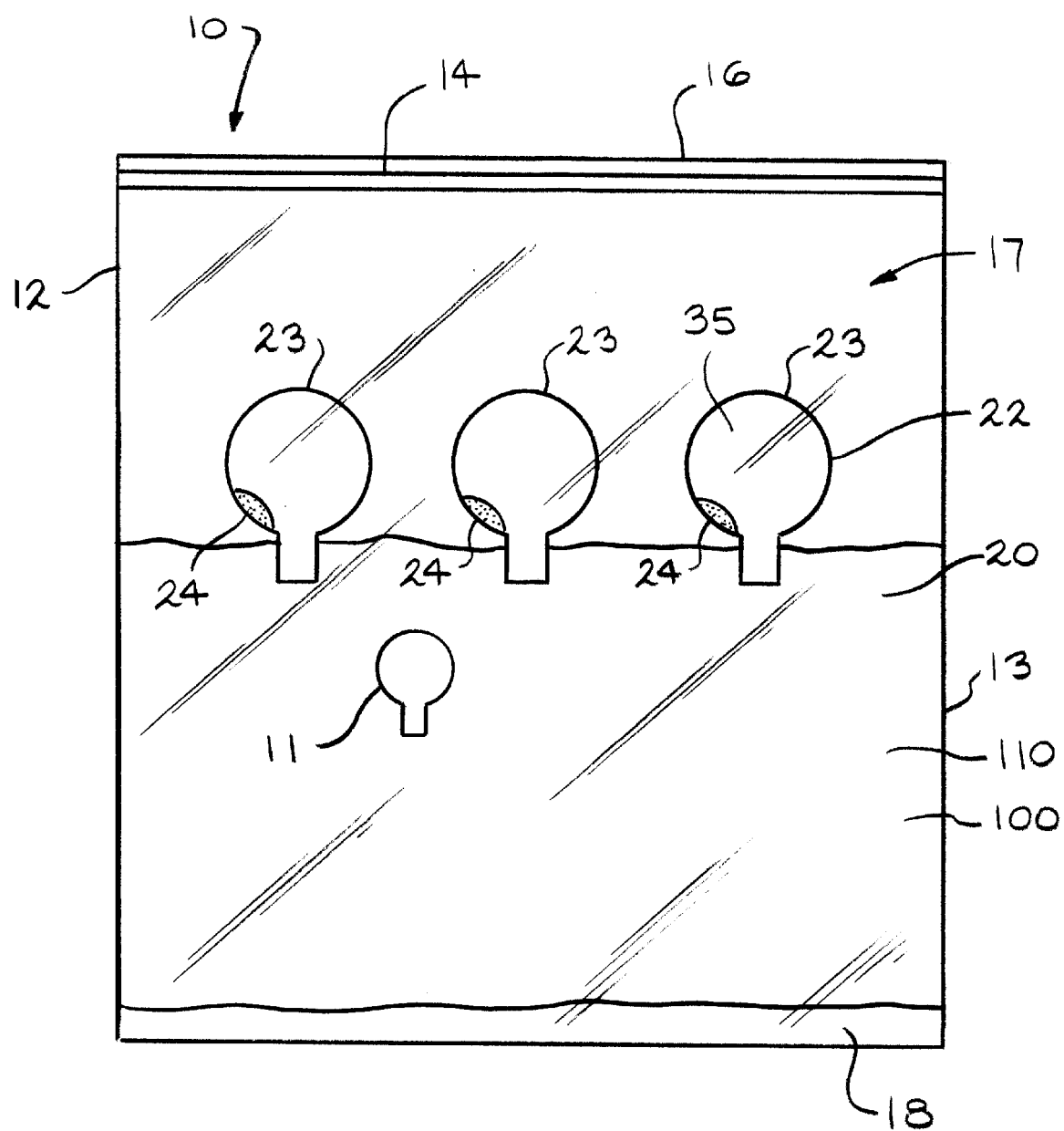
FIG. 4 shows a perspective view of the testing kit with the container loaded with the aqueous solution to be tested.

As shown in FIG. 4, the aqueous solution to be tested 20, which may or may not harbor microorganisms 110, is loaded into the plastic bag 13.

In a second embodiment, a suspension to be tested 100, which may or may not harbor microorganisms 110, is loaded into the plastic bag 13, as seen in FIG. 4. In this second embodiment, a suspension to be tested 100 replaces the aqueous solution to be tested 20. The suspension to be tested 100 may be embodied to comprise, for example, sterile water mixed with soil, milk, or a piece of food like hamburger or chicken. The types of possible suspensions is well known to those skilled in the art.

In a third embodiment, both an aqueous solution to be tested 20, and a suspension to be tested 100, are loaded into the plastic bag 13 simultaneously.

Thus, the testing kit 10 has the versatility to test for the presence of microorganisms 110 in an aqueous solution to be tested 20, a suspension to be tested 100, or both at the same time, all within the same plastic bag 13. The manner of testing is more fully described below.

In an embodiment of the testing kit 10, the medium 18 and aqueous solution to be tested 20, or suspension to be tested 100, or both, are placed in the plastic bag 13 and kept at around 37 Degrees Centigrade for 24 hours. This allows any microorganisms 110 in the aqueous solution to be tested 20, or suspension to be tested 100, to feed on the medium 18 and multiply many times over, thus making their detection in the at least one reaction chamber 22 more efficient (requiring less time and fewer expensive reagents) (FIG. 1). It is noted that in other embodiments, different temperatures may be equally useful depending on the optimal growth requirements of the microorganisms 110 to be tested.

The medium 18 may be embodied as comprising a variety of nutrient rich sugars, proteins, and mixtures thereof. A typical growth medium in the plastic bag 13 could contain tryptose, sodium chloride, sorbitol, tryptophan, di-potassium hydrogen phosphate, potassium dihydrogen phosphate, and lauryl sulphate sodium salt plus IPTG (1-Isopropyl-beta-D-1-thiogalactopyranoside). IPTG is an enzyme inducer that induces members of the coliform group of bacteria, if they are present in the aqueous solution to be tested 20, or suspension to be tested 100, to excrete enzymes. As described below, the kit 10 can detect the presence of these enzymes.

Additional examples of mediums 18 for promoting the growth of salmonella and listeria are described in U.S. Pat. No. 5,145,786 to Bailey et al., which is incorporated herein by reference.

Shown in FIG. 4 is the aqueous solution to be tested 20 mixing with the medium 18. Of course, as described above, a suspension to be tested 100 could replace the aqueous solution to be tested 20, as indicated in FIG. 4, or both an aqueous solution to be tested 20 and suspension to be tested 100 may be loaded into the bag 13.

FIG. 1 also shows at least one reaction chamber 22 located in the bag interior 17. While the present testing kit 10 will work with at least one reaction chamber 22, it may be embodied with a plurality of reaction chambers 23 as shown in FIGS. 1, 2, 4. This allows the sequential testing for different microorganisms 110 all within the same plastic bag 13, without cross contamination between the reaction chambers 23, as fully described below.

The at least one reaction chamber 22 may be embodied and constructed of a resilient material. That is, it can be deformed when pressure is applied to it, and then return to its predeformed state when the pressure is relieved. The resilient material may be plastic, but could be constructed of other materials with similar properties, such materials known to those skilled in the art. The at least one reaction chamber 22 has a reactive agent 24 contained therein, the reactive agent 24 is for detecting the presence of microorganisms 110. The reactive agent 24 may be a plurality of different chromogens or chromogenic substrates. That is, materials that change color when brought into contact with or mixed with, microorganisms 110, enzymes, microorganism 110 excretions, and so forth. Such reactive agents 24 being well known to those skilled in the art.

Figure 5:
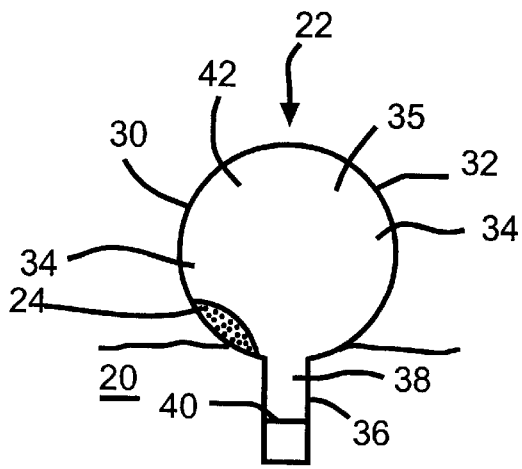
FIG. 5 shows a perspective view of the rupturable membrane reaction chamber prior to the rupturable membrane being ruptured.

For example, in FIG. 5, the reactive agent 24 in the rupturable membrane reaction chamber 30 may be embodied to contain a chemical such 5-Bromo-4-chloro-03-indoxyl-beta-D-galactopyranoside ("BCIG"). If any coliform bacteria grows in the aqueous solution to be tested 20, it would excrete the enzyme Beta-D-galactosidase. When this mixes with BCIG in the reaction chamber 30 the BCIG is cleaved by the enzyme, and when so cleaved, a blue-green coloration develops in the aqueous solution to be tested 20. In this example, BCIG determines the presence of members of the coliform group of bacteria.

As shown in FIGS. 1 and 2, a plurality of reaction chambers 23 are provided for in the testing kit 10. The reason for a plurality of reaction chambers 23, is that it is often desirous to test for many different microorganisms 110 in an aqueous solution to be tested 20, or a suspension to be tested 100, and this calls for a different reactive agent 24 for detecting the presence of each different microorganism 110. Thus, while the reactive agent 24 BCIG determines the presence of the coliform group of bacteria, distinct reactive agents 24 loaded into each of the plurality of reaction chambers 23 could test for distinct microorganisms 110.

For example, in FIG. 1, the first of the plurality of reaction chambers 23a could test for coliform bacteria as described above. Next, the second of the plurality of reaction chambers 23b could test to determine if any of the coliform bacteria were members of the *E. coli* group of bacteria. To do this, in the second of a plurality of reaction chambers 23b the chromogenic reactive agent 24 may be embodied as X-Glucuro CHA salt. This chromogen 24 can be cleaved by a second enzyme known as Beta-D-glucuronidase. This enzyme is excreted by any *E. coli* bacteria that may be present in the aqueous solution to be tested 20. In this scenario, a blue color will develop, when the aqueous solution to be tested 20 is drawn into the reaction chamber 23b, confirming the presence of *E. coli* bacteria by the presence of first a blue-green color in the first of the plurality of reaction chambers 23a, followed by a blue color in the second of the plurality of reaction chambers 23b.

Additionally, a third test, for example, to determine the presence of salmonella may be conducted in the third of the plurality of reaction chambers 23c. Contained in this third of a plurality of reaction chambers 23c is an embodiment of reactive agent 24 known to react with salmonella.

In yet another embodiment of the testing kit, the presence of listeria may be detected. In such an embodiment, one of the plurality of reaction chambers 23 may be loaded with reactive agents such as the ones described in U.S. Pat. No. 6,068,988 to Schabert et al. Listeria monocytogenes secrete phosphatidylinositol-specific phospholipase C (1-phosphatidyl-D-myo-inositol inositolphospho-hydrolase or "PI-PLC"). Cleavage of this reactive agent by bacterial PI-PLC results in mainly the formation of inositol 1,2-cyclic phosphate and 5-bromo-4-chloro-3-indoxyl which, after dimersiation, may subsequently be oxidized by atmospheric oxygen or another oxidant. The result may be a deep blue indigo color.

In other embodiments of the present testing kit 10, the presence of fecal streptococcus, enterococcus, iron and sulphur bacteria, holerae, and *vibro cholerae* may be tested for in water and/or wastewater. These and other microorganisms 110 may be present in natural suspensions such as milk, to be tested 100. They may also be present in or on solid food products such as meat, chicken, fish, or plant products that, when placed in water, form an aqueous suspension to be tested 100. The testing kit 10 can be used to analyze these types of suspensions to be tested 100.

Similarly, the presence of specific microorganisms 110 and groups of microorganisms 110, for example coliforms, may be tested for on solids such as soils and or any other solid material that when placed in water will form an aqueous solution to be tested 20 and suspension to be tested 100 mixture.

Again, the reactive agent and medium for each test are well known to those skilled in the art. Similarly, the testing kit 10 may be used to test for the presence of fungi, yeasts, yersinia, campilobacter, *staphylococcus aureus, bacillus cereus* and vibrio in foods and/or beverages.

The reactive agents or chromogenic substrates 24 are typically the most expensive component of the testing kit 10. Thus, by providing the at least one reaction chamber 22 to have a volume only capable of holding about a couple of milliliters of fluid, only a small amount of chromogenic substrate 24 need be used in the at least one reaction chamber 22, thus allowing the testing kit 10 to be produced inexpensively. Similarly, since the number of microorganisms 110 in the aqueous solution to be tested 20 have been grown to a high concentration prior to activating the plurality of reaction chambers 23, the reaction time for the calorimetric reactions is rapid and sequential reactions can be carried out in a relatively short period of time.

The at least one reaction chamber 22 may be embodied in a plurality of shapes. For example, the balloon shape as shown in FIG. 1, or it may be embodied and shaped as an elongated capsule, or other shapes known to those skilled in the art. These examples of shapes for the reaction chamber 22 are only examples and are not intended to limit the scope of the testing kit 10 in any manner.

As previously described, the testing kit 10 may be used to test an aqueous solution to be tested 20 and a suspension to be tested 100, as shown in FIG. 4. The aqueous solution to be tested 20, or suspension to be tested 100, might originate from any of a variety of sources. For example, they may come from a faucet, a well, a stream, a lake, collected rain water, bottled water, water coolers in homes and/or offices, restaurants, and any other source where water is consumed. Also, the testing kit 10 allows the testing of recreational waters found at swimming holes, swimming pools, and beaches. Microorganisms 110 in recreational waters have been known to sicken people, and the testing kit 10 can be used to test the water before anyone enters the water. Waste water may also be tested as described above.

Figure 8:
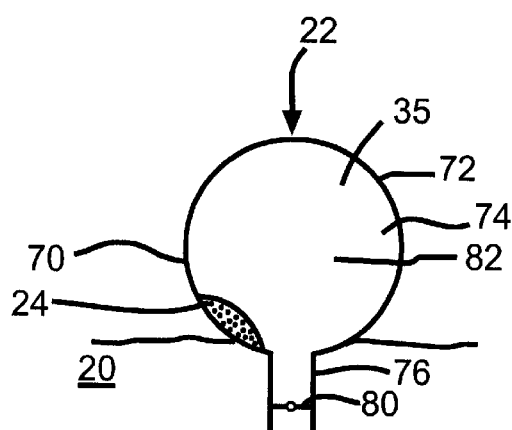
FIG. 8 shows a perspective view of the resealable aperture reaction chamber.
Figure 6:
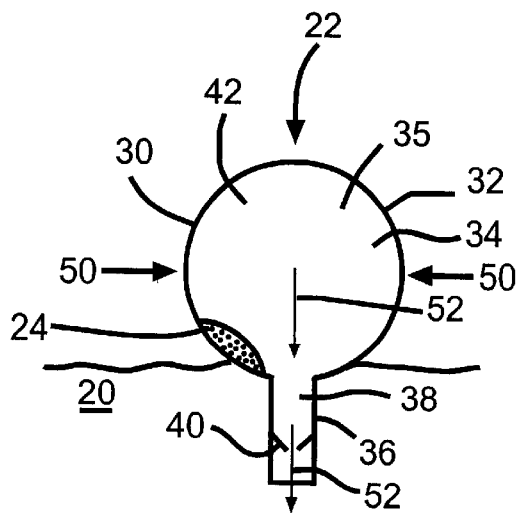
FIG. 6 show a perspective view of pressure being applied to the rupturable membrane reaction chamber shown in FIG. 5.
Figure 9:
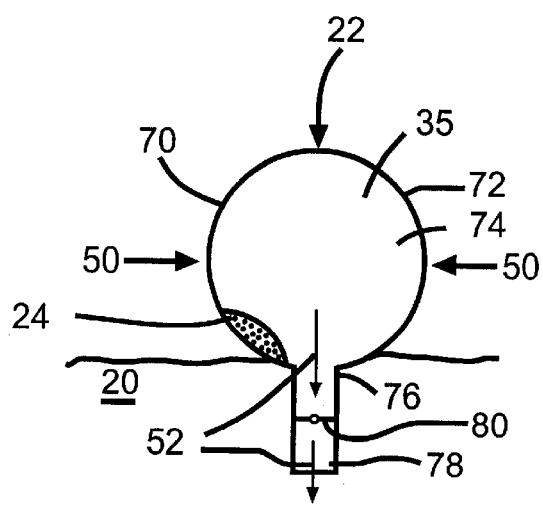
FIG. 9 shows a perspective view of pressure being applied to the resealable aperture reaction chamber of FIG. 8.
Figure 7:
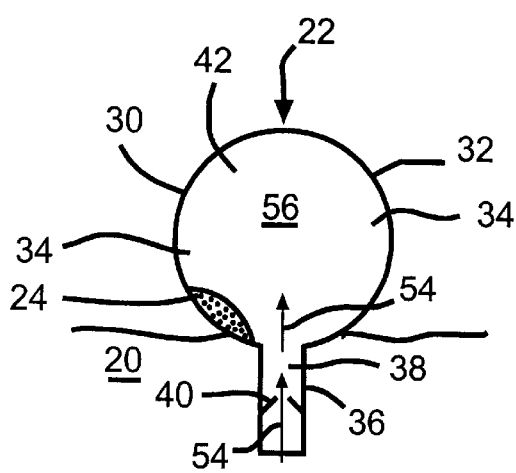
FIG. 7 shows a perspective view of the rupturable membrane reaction chamber of FIG. 6 drawing in the aqueous solution to be tested, or suspension to be tested, or both.
Figure 9A:
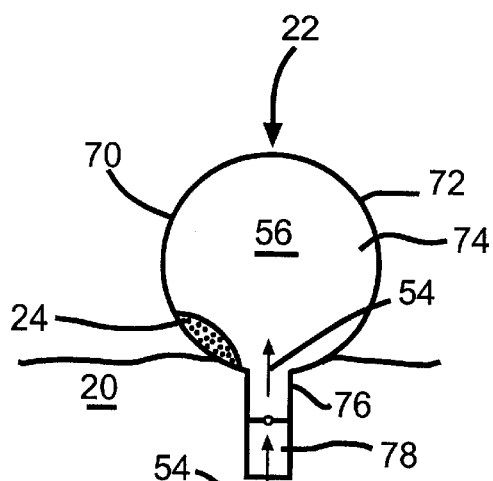
FIG. 9A shows a perspective view of the resealable aperture reaction chamber of FIG. 9 drawing the aqueous solution to be tested, suspension to be tested, or both.

The reaction chamber 22 may be embodied in a plurality of shapes, for example FIGS. 5–7 show a rupturable membrane reaction chamber 30 embodiment, and FIGS. 8–9A show the resealable aperture reaction chamber 60 embodiment. The testing kit 10 may also be embodied wherein the reaction chamber 22 is fixed to, or unattached to the bag interior 17 of the plastic bag 13.

Turning to FIGS. 5–7, the embodiment shown therein has the rupturable membrane reaction chamber 30. The rupturable membrane reaction chamber 30 has a wall 32, the wall 32 has a balloon shape but may be embodied to have other shapes. The wall 32 of the rupturable membrane reaction chamber 30 defines an airspace 34, and extending from the wall 32 is passage tube 36. The passage tube 36 defines passageway 38. Extending across the passageway 38 is a rupturable membrane 40. The airspace 34 of the rupturable membrane reaction chamber 30 may be filled with air 35 or any other suitable fluid medium, preferable gas, well known to those skilled in the art.

Also contained within the rupturable membrane reaction chamber 30 is the reactive agent 24, which as discussed above reacts when brought into contact with microorganisms 110. Prior to use, the rupturable membrane reaction chamber 30 is loaded with reactive agent 24, and the rupturable membrane 40 positioned across the passageway 38. Such procedures to accomplish this known to well known to those skilled in the art.

In use of the testing kit 10 having a rupturable membrane reaction chamber 30, the resealable opening 14 of the plastic bag 13 is opened, and the aqueous solution to be tested 20, or suspension to be tested 100, or both, are added to the plastic bag 13, and the resealable opening 14 is closed or sealed. Medium 18 is mixed with the aqueous solution to be tested 20, or suspension to be tested 100, and the microorganisms 110 in the aqueous solution to be tested 20 to feed upon the medium 18. A microbial culture in the aqueous solution to be tested 20, or suspension to be tested 100, is grown for typically 24 hours at 37° Centigrade. In other embodiments, different temperatures may be employed for growth.

After this time, the rupturable membrane reaction chamber 30 is crushed, as shown in FIG. 6 by an external pressure, depicted by arrows 50, applied to the wall 32. This causes the rupturable membrane 40 to burst. The source of the external pressure, depicted by arrows 50, would typically be the user's fingers. As shown in FIG. 6, the air 35 in the air space 34 becomes pressurized, such that it would cause the rupturable membrane 40 to burst, and the air 35 would exit the rupturable membrane reaction chamber 30 through the passageway 38 in the passage tube. This flow of the exiting air 35 is depicted by arrow 52 in FIG. 6.

Upon releasing the external pressure, depicted by arrows 50, the rupturable membrane reaction chamber 30, because it is resilient, returns to its precrushed state, and in doing so creates a vacuum or negative pressure therein. When this occurs, the aqueous solution to be tested 20, or suspension to be tested, or combination thereof, is drawn into the rupturable membrane reaction chamber 30, indicated by arrows 54 in FIG. 7. The reactive agent 24 then mixes with the aqueous solution to be tested 20, and/or suspension to be tested. This makes a test mixture 56, which may or may not result in a chromogenic change in the rupturable membrane reaction chamber 30, because such a change depends on the presence of predetermined microorganisms 110 in the aqueous solution to be tested 20, and/or suspension to be tested 100. If a chromogenic or color change occurs in the test mixture 56, the user can assess which microorganism 110 is present depending on which reactive agent 24 is in the rupturable membrane reaction chamber 30, and any colormetric changes that occur.

The rupturable membrane 38 can be constructed of sufficiently small diameter, such that when the rupturable membrane reaction chamber 30 is filled with the aqueous solution to be tested 20, and/or suspension to be tested 100, no leakage occurs from the rupturable membrane reaction chamber 30. This prevents the test mixture 56 from contaminating the remaining aqueous solution to be tested 20, or suspension to be tested 100, in the plastic bag 13. Thus each of the rupturable membrane reaction chambers 30 can be loaded with a different, distinct reactive agent 24, to conduct numerous tests on the aqueous solution to be tested 20, and/or suspension to be tested, without significant cross contamination between the rupturable membrane reaction chambers 30.

Another embodiment of the reaction chamber 22 is shown in FIGS. 8–10, which illustrates the resealable aperture reaction chamber 70 embodiment of the testing kit 10. The resealable aperture reaction chamber 70 has a wall 72 having a balloon shape, however, the wall 72 may be embodied to have a capsule shape, a spherical shape or any other shape known to those skilled in the art. The wall 72 of the resealable aperture reaction chamber 70 defines therein an airspace 74 filled with air 35 or any other suitable gas or fluid medium known to those skilled in the art. Extending from the wall 72 is passage tube 76. The passage tube 76 defines a passageway 78 therein. Positioned in the passageway 78 and extending fully across said passageway 78 is the resealable aperture 80, which is made of a resilient material such as resilient plastic, such that after it is deformed, it is able to automatically returns to its predeformed state.

Also contained within the resealable aperture reaction chamber 70 is the reactive agent 24 that reacts with microorganisms 110. Prior to use, the resealable aperture reaction chamber 70 is loaded with the reactive agent 24, and the resealable aperture 80 is closed.

To use the resealable aperture reaction chamber 70, pressure, indicated by arrows 50 in FIG. 9, is applied to the wall 72. Again, this pressure, indicated by arrows 50, is typically applied by the user's fingers. As the pressure, indicated by arrows 50, increases the resealable aperture 80 expands and opens, and air 35 is forced out of the airspace 74. This air 35 proceeds through the resealable aperture 80 and the passageway 78 in the passage tube 76. Arrows 52 in FIG. 9 indicated the air 35 exiting the resealable aperture reaction chamber 70.

In FIG. 9A, the pressure, indicated by arrows 50, is relieved, thus not shown in FIG. 9A, and the resealable membrane reaction chamber 70 returns to its prior balloon shape, and in doing so draws the aqueous solution to be tested 20, or suspension to be tested 100, into the resealable aperture reaction chamber 70 indicated by arrows 54. This occurs due to the vacuum or negative pressure generated as the resealable membrane reaction chamber 70 returns to predeformed state as shown in FIG. 8. The resealable aperture 80 closes, thus preventing the test mixture 56 contained in the resealable aperture reaction chamber 70 from leaking, and cross-contaminating any of the other plurality of reaction chambers 23.

Just as with the rupturable membrane reaction chamber 30, chromogenic changes in the test mixture 56 in the resealable aperture reaction chamber 70 may be analyzed for the detection of microorganisms 110.

The testing kit 10 may also be embodied to have a plurality of both rupturable membrane reaction chambers 30 and resealable aperture reaction chambers 70, in the plastic bag 13 at the same time. This is due to the fact that there is no cross contamination between the rupturable membrane reaction chambers 30 and the resealable aperture reaction chambers 70.

Another embodiment of the present invention provides for a sequential narrowing process to be used for testing the presence of a specific microorganism, for example a pathogenic variant of the coliform group of bacteria. In this embodiment, separation of specific enzymatic, and biochemical reactions for positive identification of a given species is possible, for example, *E. coli* identified by the presence of both galactosidase and glucoronidase enzymes, or the positive identification of a specific strain of bacteria or pathovar, such as *E. coli* 0157.

For example, a narrowing process may be used to detect *E. coli* bacteria. First, the plastic bag 13 is loaded with three reaction chambers 22 having different reactive agents 24 contained therein, either rupturable membrane reaction chambers 30 or resealable aperture reaction chambers 70, may be used. The plastic bag 13 is also loaded with the medium 18 and the suspect aqueous solution to be tested 20.

The first of the three reaction chambers 22 is crushed, and if there is no reaction, then the specific microorganism 110 being sought is not present. However, if upon crushing there is a reaction in the reaction chamber 22, then it is known that the generic coliform group of bacteria is present, and the testing continues.

The type of bacteria is further narrowed by crushing the next reaction chamber 22. If there is no reaction, the specific type of bacteria being testing for is not present. If a reaction does occur, that narrows the range of the coliform group of bacteria present, and the testing continues.

The last of the reaction chambers 22 is crushed, and if there is no reaction, this indicates that a pathogenic form of coliform bacteria is not present. If, however, there is a reaction, a pathogenic member of the coliform group of bacteria has been detected, such as *E. coli*, and the user is placed on alert, as this form of the bacteria may be deadly if consumed. The reactive agents 24 used in such sequential testing as described herein, being well known to those skilled in the art.

The testing kit 10 may also have a kill pod 11, as shown in FIG. 1, having a sufficient dose of chemicals to kill most, if not all, microorganisms 110. The kill pod 11 may be embodied as a crushable plastic capsule loaded with chemicals and other materials that destroy microorganisms 110. The user need only manually crush the kill 11 pod to release the chemicals at the end of the testing to destroy the microorganisms 110 in the aqueous solution to be tested 20, or suspension to be tested 100. This step renders the kit 10 safe for disposal following its use to detect potentially pathogenic microorganisms.

The testing kit 10 also provides for a methodology to use the kit. The method entails multiple steps, for example, the first step requires providing a container 12 which may be embodied as a plastic bag 13. Second, opening a resealable opening 14 of the container. Third, depositing a medium 18 in the plastic bag 13. Fourth, placing at least one reaction chamber 22 having a reactive agent 24 contained therein in the plastic bag 13. This reaction chamber 22 may be a rupturable membrane reaction chamber or a resealable aperture reaction chamber. Fifth, adding the aqueous solution to be tested 20, or suspension to be tested, to the plastic bag 13, or both. Sixth, closing the resealable opening 14 in the plastic bag 13. Seventh, sealing the plastic bag 13. Eighth, mixing the medium 18 with the aqueous solution to be tested 20, or suspension to be tested. Ninth, rupturing the rupturable membrane reaction chamber 30 or opening the resealable aperture reaction chamber 70, or both, depending on which embodiment is being utilized, so that the aqueous solution to be tested 20, or suspension to be tested, in the plastic bag 13 mixes with the reactive agent 24. Tenth, examining the test mixture 56 for chromogenic changes. And finally, crushing the kill pod 11 to destroy any the microorganisms 110 present in order to render the kit safe for disposal. All of these steps do not have to be done to utilize the present invention, for example, the use of a kill pod may be unnecessary in all applications.

It is noted that the embodiments of testing kit 10 are in no way limited to the detection of deleterious microorganism 110. The present testing kit 10 may be embodied to detect the presence of beneficial microorganisms 110 as well. Beneficial microorganisms 110 may be defined as microorganisms 110 that are beneficial to humans and animals, for example, yeasts for breads and beverages, bacteria for cheeses, bacteria in digestive tracts, etc. The testing kit 10 may be embodied to have the requisite reactive agent 24 and medium 18 to test for the presence of such beneficial microorganisms 110 without departing from the matter disclosed herein and the principles of the testing kit 10. Such matching of the reactive agent 24 to the microorganism 110 to be tested, being well known to those skilled in the art.

Thus, the present testing kit 10 provides an inexpensive, easy use, reliable, and quick way to test for a plurality of microorganisms 110.

It is understood that, while the invention has been described in detail herein, the invention can be embodied otherwise without from the principles thereof. All of these other embodiments are meant to come within the scope of the present testing kit and methodology as defined in the claims.

What is claimed:

1. A testing device for testing an aqueous solution and/or suspension for the presence microorganisms, the device comprising:
    a) a container, the container comprising a bag that defines a bag interior therein, the bag comprising an edge having a resealable opening, the resealable opening providing access to the bag interior;
    b) a medium, the medium loadable into the bag through the resealable opening, the medium for promoting the growth of microorganisms in the aqueous solution and/or suspension;
    c) a rupturable membrane reaction chamber loadable into the bag through the resealable opening and positionable in the bag interior, and unattached to the bag so as to be freely movable about the bag interior, the rupturable membrane reaction chamber made of resilient material and for carrying out chemical reactions therein, the rupturable membrane reaction chamber further comprises a passage tube extending therefrom, the passage tube defining a passageway, and a rupturable membrane seals the passage tube and is rupturable upon crushing the rupturable membrane reaction chamber, so that when the rupturable membrane reaction chamber is crushably released, the rupturable membrane ruptures and the aqueous solution and/or suspension to be tested is drawn into the rupturable membrane reaction chamber; and
    d) a reactive agent disposed in the rupturable membrane reaction chamber for detecting the presence of at least one microorganism when brought into contact with the aqueous solution and/or suspension to be tested.

2. The testing device of claim 1 wherein the microorganisms being testing for are selected from the group consisting of bacteria, the coliform group of bacteria, the *E.coli* group of bacteria, salmonella bacteria, listeria, fungi, yeasts, viruses, yersinia, campilobacter, *staphylococcus aureus, bacillus cereus* and vibrio.

3. The testing device of claim 1 wherein the diameter of the passage tube is sufficiently small so that when the rupturable membrane reaction chamber is filled with the aqueous solution and/or suspension, the rupturable membrane substantially reseals itself, so that the aqueous solution and/or suspension in the bag is not contaminatable by the reactive agent.

4. The testing device of claim 3 further comprising a plurality of rupturable membrane reaction chambers each of which is loaded with at least one reactive agent to test for the presence of a predetermined microorganism.

5. The testing device of claim 1 further comprising a plurality of rupturable membrane reaction chambers wherein each of the plurality of rupturable membrane reaction chambers holds therein a distinct reactive agent to test for the presence of a predetermined microorganism.

6. The testing device of claim 1 wherein the container is a resealable clear plastic bag, and wherein the medium has a state selected from the group consisting of: pastes, pellets, powders, and liquids.

7. The testing device of claim 1 further comprising a kill pod having microorganism killing agents releaseable upon crushing the kill pod.

8. A device for testing an aqueous solution and/or suspension for the presence of microorganisms, the device comprising:
    a) a container;
    b) a medium loadable in the container for promoting the growth of microorganisms;
    c) at least one reaction chamber located in the container;
    d) a reactive agent disposed in the at least one reaction chamber for detecting the presence of at least one microorganism when brought into contact with the aqueous solution and/or suspension to be tested;
    e) wherein the at least one reaction chamber is made of resilient material; and
    f) wherein the at least one reaction chamber has a resealable aperture which opens when sufficient pressure is exerted on the at least one reaction chamber, and closes when pressure is removed from the at least one reaction chamber, allowing the aqueous solution and/or suspension to be drawn therein and contact the reactive agent held in the at least one reaction chamber.

9. A device for testing an aqueous solution for the presence of microorganisms, the device comprising:
    a) a container;
    b) a medium loadable in the container for promoting the growth of microorganisms;
    c) a plurality of reaction chambers loadable in the container;
    d) at least one reactive agent contained within each of the plurality of reaction chambers for detecting the presence microorganisms when brought into contact with the aqueous solution and/or suspension;
    e) wherein the plurality of reaction chambers are made of resilient material;
    f) wherein each of the plurality of reaction chambers has a resealable aperture which opens when sufficient pressure is exerted on the at least one reaction chamber, and closes when pressure is removed from the at least one reaction chamber, thus allowing the aqueous solution and/or suspension to be drawn therein and contact the reactive agent in the at least one reaction chamber; and
    g) wherein the reactive agent in each of the plurality of reaction chambers is for testing for the presence of a predetermined microorganism.

10. A device for testing an aqueous solution and/or suspension for the presence of one or more microorganisms, the device comprising:
    a) a container;
    b) a medium loadable in the container and for promoting the growth of microorganisms;
    c) a plurality of reaction chambers positionable in the container;
    d) a reactive agent disposed in the each of the plurality of reaction chambers for detecting the presence of at least one microorganism when brought into contact with the aqueous solution to be tested;

e) wherein the plurality of reaction chambers are made of resilient material; and f) wherein each of the plurality of reaction chambers has a resealable aperture which opens when sufficient pressure is exerted on thereon, and closes when pressure is removed therefrom, thus allowing the aqueous solution and/or suspension to be drawn therein and contact the reactive agent held therein;

g) wherein the reactive agent loadable into each of the plurality of reaction chambers is a distinct reactive agent to test for the presence of predetermined microorganisms, allowing for the testability of a plurality of microorganisms.

11. A device for testing an aqueous solution and/or suspension for the presence of microorganisms, the device comprising:

a) a container;

b) a medium loadable in the container for promoting the growth of microorganisms;

c) at least one reaction chamber loadable in the container, the at least one reaction chamber defining an interior;

d) a reactive agent disposed in the at least one reaction chamber interior and for detecting the presence of at least one microorganism when brought into contact with the aqueous solution and/or suspension;

e) wherein the at least one reaction chamber is made of resilient material;

f) wherein the at least one reaction chamber has a resealable aperture which opens when sufficient pressure is exerted on the at least one reaction chamber, and closes when pressure is removed from the at least one reaction chamber, allowing the aqueous solution and/or suspension to be drawn therein and contact the reactive agent held in the at least one reaction chamber; and g) wherein the at least one reaction chamber is unattached to the container when in the container interior, allowing the at least one reaction chamber freely moveable about the container interior.

12. A testing device for testing an aqueous solution and/or suspension for microorganisms comprising:

a) a container comprising a transparent material;

b) a medium loadable in the container for promoting the growth of microorganisms;

c) at least one reaction chamber made of a transparent resilient material and containing a reactive agent loadable into the container;

d) the reactive agent disposed in the at least one reaction chamber for detecting the presence of at least one microorganism when brought into contact with the aqueous solution and/or suspension to be tested; and e) wherein the at least one reaction chamber has a resealable aperture which opens when sufficient pressure is exerted on the at least one reaction chamber, and closes when pressure is removed from the at least one reaction chamber, thus allowing the aqueous solution and/or suspension to be tested to be drawn therein and contact the reactive agent in the at least one reaction chamber; and f) wherein the container and the at least one reaction chamber are made of transparent material so that colorimetric changes therein are observable.

13. A testing device for testing an aqueous solution and/or suspension for microorganisms comprising:

a) a container;

b) a medium deposited in the container for promoting the growth of microorganisms;

c) a reaction chamber comprising a balloon shape positionable in the container, the reaction chamber further comprising a tube extending therefrom;

d) a reactive agent internally disposed in the at least one reaction chamber and for detecting the presence of at least one microorganism when brought into contact with the aqueous solution and/or suspension to be tested, the reaction chamber is of a made of resilient material;

e) wherein the at least one reaction chamber has a resealable aperture positionable in the tube, the resealable aperture openable when sufficient pressure is exerted on the reaction chamber, and closes when pressure is removed from the reaction chamber, thus allowing the aqueous solution and/or suspension to be drawn therein through the tube and contact the reactive agent in reaction chamber; and f) wherein the reactive agent is for testing for the presence of predetermined microorganisms.

14. A testing device for testing an aqueous suspension and/or solution for microorganisms comprising:

a) a container;

b) a medium loadable in the container for promoting the growth of microorganisms;

c) a plurality of reaction chambers each comprising walls and positionable internal to the container, each reaction chamber defining an interior;

d) a reactive agent loadable into each of the plurality of reaction chambers interiors for detecting the presence of at least one microorganism when brought into contact with the aqueous solution and/or suspension to be tested, the reaction chamber is of a made of resilient material and has the reactive agent contained therein;

e) wherein each of the plurality of reaction chambers has a resealable aperture which opens when sufficient pressure is exerted on each of the plurality of reaction chamber walls, and closes when pressure is relieved, thus allowing the aqueous solution and/or suspension to be drawn into each of the plurality of reaction chamber interiors and contact the reactive agent disposed therein; and f) wherein the reactive agent loadable into each of the plurality of reaction chambers is distinct so the presence of predetermined microorganisms is testable.

15. A testing device for testing an aqueous solution and/or suspension for microorganisms comprising:

a) a container comprising a resealable opening;

b) a medium loadable in the container through the resealable opening and for promoting the growth of microorganisms;

c) a plurality of reaction chambers positionable in the container, each loadable with a different chromogentic substrate;

d) a reactive agent disposed in the at least one reaction chamber for detecting the presence of at least one microorganism when brought into contact with the aqueous solution and/or suspension to be tested;

e) wherein the at least one reaction chamber is made of resilient material and holds the reactive agent therein; and f) wherein the at least one reaction chamber is unattached to the interior of the container, and is freely movable about the interior of the container, and g) wherein each of the plurality of reaction chambers has an internal volume of about 2.0 milliliters and each is releaseably crushable so that the aqueous solution and/or suspension is drawn therein and contacts the chromogenic substrate so that colorimetric changes are observable.

16. A testing device for testing an aqueous solution and/or suspension for microorganisms comprising:

a) a container;

b) a medium deposited in the container for promoting the growth of the microorganisms;

c) at least one reaction chamber loadable in the container;

d) a reactive agent disposed in the at least one reaction chamber for detecting the presence of at least one microorganism when brought into contact with the aqueous solution and/or suspension to be tested;

e) wherein the at least one reaction chamber is made of resilient material and defines an airspace and filled with a gas therein;

f) wherein the at least one reaction chamber has a resealable aperture which opens when sufficient pressure is exerted on the at least one reaction chamber, and closes when pressure is removed from the at least one reaction chamber, so that upon releasable crushing the at least one reaction chamber the gas is forced out of the at least one reaction chamber through the resealable aperture, and upon releasing the at least one reaction chamber a negative pressure develops therein drawing the aqueous solution and/or suspension therein so that it contacts the reactive agent in the at least one reaction chamber; and g) wherein the reactive agent comprises a chromogenic substrate providing for colorimetric changes in the presence of microorganisms.

17. A testing device for testing an aqueous solution and/or suspension for microorganisms comprising:

a) a container;

b) a medium deposited in the container for promoting the growth of microorganisms;

c) a plurality of reaction chambers located in the container made of a transparent resilient material, wherein each reaction chamber defines a volume of about 2 milliliters;

d) a reactive agent disposed in each of the plurality of reaction chambers for detecting the presence of at least one microorganism when brought into contact with the aqueous solution and/or suspension to be tested;

e) the plurality of reaction chambers each having a resealable aperture which is openable when a sufficient pressure is exerted on the at least one reaction chamber, and closeable when the sufficient pressure is relieved, thus allowing the aqueous solution and/or suspension to be drawn therein and contact the reactive agent held therein; and f) wherein the resilient material from which each of the plurality of reaction chambers is made provides for the tight resealing of the resealable aperture after is fills with the aqueous solution/suspension to be tested, preventing any backflow into the container through the resealable aperture and keeping the aqueous solution and/or suspension in the container from being contaminated with the reactive agent; and g) wherein each of the plurality of resealable aperture reaction chambers is loadable with at least one reactive agent to test for the presence of a predetermined microorganism.

18. A testing device for testing an aqueous solution and/or suspension for microorganisms comprising:

a) a resealable container defining a container interior, the container for holding the aqueous solution and/or suspension;

b) a medium loadable in the container for promoting the growth of microorganisms, c) a plurality of reaction chambers loadable in the container and freely movable about the container interior each for allowing a testing for different microorganisms;

d) a reactive agent disposed in each of the plurality of reaction chambers for detecting the presence of at least one microorganism when brought into contact with the aqueous solution and/or suspension;

e) wherein each of the plurality of reaction chambers is made of resilient plastic material;

f) and wherein at least one of the plurality of reaction chambers comprises rupturable membrane reaction chamber comprising a rupturable membrane, and wherein at least one of the plurality of reaction chambers comprises a resealable aperture reaction chamber comprising a resealable aperture;

g) wherein upon crushably releasing the rupturable membrane reaction chamber the rupturable membrane reaction chamber bursts due to excessive pressure therein, exposing the reactive agent held therein to the aqueous solution and/or suspension to be tested;

h) wherein upon crushably releasing the resealable aperture reaction chamber, the resealable aperture is openable and closeable, drawing in the aqueous solution and/or suspension therein and exposing it to the reactive agent held therein; and i) the device further comprising a kill pod containing a material for killing any microorganisms present in the resealable container.

19. The testing device according to claim 18 wherein each of the plurality of reaction chambers has a distinct reactive agent to test for the presence of a predetermined microorganism therein.

* * * * *